US012748104B2

(12) United States Patent
Carnes et al.

(10) Patent No.: US 12,748,104 B2
(45) Date of Patent: Sep. 29, 2026

(54) METHOD FOR DETECTING POLYSORBATES

(71) Applicant: GLAXOSMITHKLINE INTELLECTUAL PROPERTY DEVELOPMENT LIMITED, Stevenage (GB)

(72) Inventors: Katie A. Carnes, King of Prussia, PA (US); Justin W. Shearer, King of Prussia, PA (US)

(73) Assignee: GlaxoSmithKline Intellectual Property Development Limited, Stevenage (GB)

( * ) Notice: Subject to any disclaimer, the term of this patent is extended or adjusted under 35 U.S.C. 154(b) by 904 days.

(21) Appl. No.: 17/912,223

(22) PCT Filed: Mar. 17, 2021

(86) PCT No.: PCT/IB2021/052228

§ 371 (c)(1),
(2) Date: Sep. 16, 2022

(87) PCT Pub. No.: WO2021/186363

PCT Pub. Date: Sep. 23, 2021

(65) Prior Publication Data

US 2023/0184750 A1 Jun. 15, 2023

Related U.S. Application Data

(60) Provisional application No. 62/992,295, filed on Mar. 20, 2020.

(51) Int. Cl.
*G01N 30/88* (2006.01)
*G01N 33/53* (2006.01)

(52) U.S. Cl.
CPC ......... *G01N 33/5308* (2013.01); *G01N 30/88* (2013.01); *G01N 2030/8831* (2013.01); *G01N 2400/00* (2013.01)

(58) Field of Classification Search
CPC ............... G01N 33/5308; G01N 30/88; G01N 2030/8831; G01N 2400/00; G01N 33/92
See application file for complete search history.

(56) References Cited

U.S. PATENT DOCUMENTS

| | | | | |
|---|---|---|---|---|
| 2007/0082004 A1* | 4/2007 | Morton | C07K 1/30 | 530/391.1 |
| 2012/0225487 A1* | 9/2012 | Weber | G01N 33/50 | 436/93 |
| 2019/0212258 A1 | 7/2019 | Harrison et al. | | |

FOREIGN PATENT DOCUMENTS

| | | |
|---|---|---|
| WO | WO-2004099234 A2 | 11/2004 |
| WO | WO-2013003575 A1 | 1/2013 |
| WO | WO 2013/175312 A1 | 11/2013 |
| WO | WO-2014160497 A1 | 10/2014 |

OTHER PUBLICATIONS

Agilent ZORBAX Rapid Resolution High Definition SB-CN Column Agilent Technologies, Inc., 2011 (Year: 2011).*

(Continued)

*Primary Examiner* — Jennifer Wecker
*Assistant Examiner* — Steven Ray Castaneda
(74) *Attorney, Agent, or Firm* — Wei Huang

(57) ABSTRACT

The present invention relates to provision of a method for detection of polysorbate in pharmaceutical products.

20 Claims, 9 Drawing Sheets

(56) References Cited

OTHER PUBLICATIONS

Dixit et al., "Residual Host Cell Protein Promotes Polysorbate 20 Degradation in a Sulfatase Drug Product Leading to Free Fatty Acid Particles," J. Pharm. Sci., vol. 105, (2016), pp. 1657-1666.
Labrenz S.R., "Ester hydrolysis of polysorbate 80 in mAb drug product: Evidence in support of the hypothesized risk after the observation of visible particulate in mAb formulations", J. Pharm. Sci., vol. 103, No. 8, pp. 2268-2277 (2014).
Martos, et al., "Trends on analytical characterization of polysorbates and their degradation products in biopharmaceutical formulations", J. Pharm. Sci., vol. 106, No. 7, pp. 1722-1735 (2017).
Loughrill et al., "An investigation into the fatty acid content of selected fish-based commercial infant foods in the UK and the impact of commonly practiced re-heating treatments used by parents for the preparation of infant formula milks", Food Chem., vol. 197, pp. 783-789 (2016).
Degterev et al., "A development of high-throughput HPLC method for the polysorbate 80 quantitation in protein therapeutic products", J. Chromatogr. B, vol. 1133, 121847, pp. 1-11 (2019).
Carnes K.A., et al., "A Platform Analytical Method for Intact Polysorbates in Protein-containing Biopharmaceutical Products via HPLC-CAD," Journal of Liquid Chromatography & Related Technologies, 2022, vol. 45(17-20), pp. 259-270, Retrieved from [https://doi.org/10.1080/10826076.2023.2207024].
International Search Report and Written Opinion for International Application No. PCT/IB2021/052228, mailed Jun. 30, 2021, 13 Pages.
Wang H., "Study on the Detection of Tween80 Content in Protein Preparations," Hebei Chemical Industry, vol. 34(3), pp. 44-47(5 Pages).

* cited by examiner

METHOD FOR DETECTING POLYSORBATES

This application is a 371 of International Application No. PCT/IB2021/052228 filed Mar. 17, 2021, which claims the benefit of U.S. Provisional Application No. 62/992,295 filed Mar. 20, 2020, the disclosures of which are incorporated herein in their entireties.

FIELD OF THE INVENTION

The present invention relates to provision of a method for detection of polysorbate in pharmaceutical products.

BACKGROUND OF THE INVENTION

Polysorbates are commonly used non-ionic surfactants in both food and biopharmaceutical products. In biopharmaceutical products, they may be used to prevent protein adsorption to surfaces, aggregation, and particle formation. However there are concerns that degradation products of such polysorbates could cause issues when used in parenterals, for example injection site irritation. Because of this use, great interest lies in the development of analytical methods to monitor the integrity of polysorbates, specifically polysorbate 80 (polyoxyethylene sorbitan monooleate). Commercially available PS80 is heterogenous, with the most common process related subspecies being polyoxyethylene (POE) groups, POE isosorbide mono-ester, and POE sorbitan/isosorbide di-, tri-, tetra-esters; thus, the development of an analytical method has been challenging. Several methods have been reported.

None of these provide: (1) specificity-immunity of the PS80 mono-ester peak enables quantification in degraded samples; (2) sensitivity, ≤20 ppm; (3) accuracy, 95-105%; (4) precision, ≤5%; (5) transferability, including quality control (QC); (6) the ability to validate in a similar amount of time and at approximately the same cost as traditional UV-Visible high performance liquid chromatography (HPLC) methods; (7) the ability to monitor intact and degraded PS80 and related subspecies; (8) the ability to serve as a platform method for protein-containing biopharmaceutical formulations; (9) linearity, $R^2>0.99$; (10) resolution of fatty acids; (11) mass-spectrometry translatable; (12) does not employ derivatization; and/or (13) does not utilize quantification that is dependent upon micelle encapsulation.

Accordingly, there is a need to provide an improved method for polysorbate detection which addresses the deficiencies detailed above and/or which can detect intact polysorbate and/or degraded polysorbate products.

SUMMARY OF INVENTION

The present invention therefore provides methods for the detection of polysorbate, for example of intact polysorbate and/or degraded polysorbate products, in a sample such as a sample containing protein e.g. of a pharmaceutical protein product such as an antigen binding polypeptide (e.g., monoclonal antibody (mAb).

Hence in a first aspect of the invention there is provided a method of identifying polysorbate e.g. intact polysorbate and/or degraded polysorbate products, in a sample containing protein, comprising subjecting said sample to the following steps: (i) precipitating the protein by exposing said sample to an organic protic polar solvent or an organic aprotic polar, (ii) separating the protein from the precipitated sample by centrifuging the precipitated sample to pellet the protein and obtaining a liquid supernatant, (iii) separating the polysorbates by subjecting the supernatant to chromatography, wherein the chromatography comprises applying the supernatant to a stationary phase column comprising an immobilised cyano group, and eluting the bound polysorbates using a mobile phase composition gradient, and (iv) detecting the separated polysorbates using a chromophore-lacking detector to identify polysorbate.

In a second aspect the present invention provides a method for identification of a protein sample(s) e.g. from a plurality of proteins, wherein said identified protein sample(s) contains from about 10 ppm to about 5000 ppm of intact polysorbate, and which comprises the following steps:

(a) measuring polysorbate in said protein samples, comprising the following steps:
 (i) precipitating the protein by exposing said sample to an organic protic polar solvent or an organic aprotic polar solvent,
 (ii) separating the protein from the precipitated sample by centrifuging the precipitated sample to pellet the protein or peptide and obtaining a liquid supernatant,
 (iii) separating the polysorbates by subjecting the supernatant to chromatography, wherein the chromatography comprises applying the supernatant to a stationary phase column comprising an immobilised cyano group, and eluting the bound polysorbates using a mobile phase composition gradient, and
 (iv) detecting the separated polysorbates using a chromophore-lacking detector to identify polysorbate;
 (b) Identifying the protein sample(s) from (a) which have levels of intact polysorbate such as PS80 which are between about 10 ppm to about 5000 ppm;

(c) Isolation and recovery of said protein(s) identified in step (b).

Also provided is a protein obtained or obtainable by the method of the second aspect of the invention and also use of said protein in medicine e.g. in preparation of a pharmaceutical formulation for administration to a human subject.

In an embodiment of the first and second aspects of the invention the method provided is a method of identifying polysorbate 80 (e.g. intact and/or degraded PS80 polysorbate) in a sample containing protein e.g. an antibody sample such as a mAb.

The steps of precipitating and separating combined with elution allows the separation of the polysorbate products in the sample and the detection step allows the detection and analysis of said intact and/or degraded polysorbate products such as PS80 and/or PS60 and/or PS40 and/or PS20.

In an embodiment of the first and second aspects of the invention the method of identifying the polysorbate in a sample containing protein or peptide e.g. an antibody such as a mAb sample that is provided herein, is a quantitative method which can be used for measurement of amounts of polysorbate such as PS80 and/or PS60 and/or PS40 and/or PS20 present in said sample including measurement of intact and/or degraded products e.g. of PS80 and/or PS60 and/or PS40 and/or PS20.

DETAILED DESCRIPTION OF THE INVENTION

Figure 1:
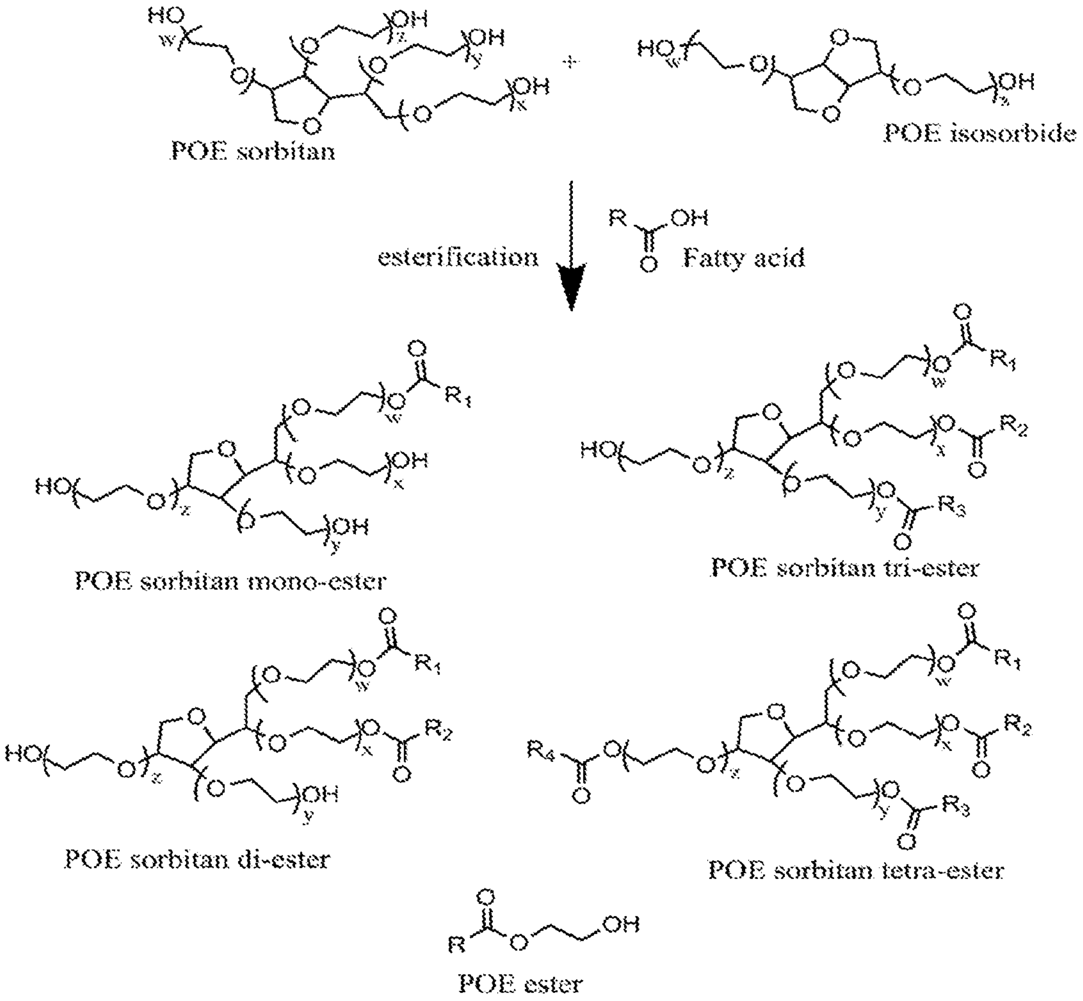
FIG. 1: shows the last two steps of the synthetic route for PS80.

Within this specification the invention has been described, with reference to embodiments, in a way which enables a clear and concise specification to be written. It is intended and should be appreciated that embodiments may be variously combined or separated without parting from the invention.

Unless defined otherwise, all technical and scientific terms used herein have the same meaning as commonly understood by one of ordinary skill in the art (e.g. in cell culture, molecular genetics, nucleic acid chemistry, hybridization techniques and biochemistry). Standard techniques are used for quantitative analytical methods.

All publications, including but not limited to patents and patent applications, cited in this specification are herein incorporated by reference as though fully set forth.

"Protein", "Polypeptide," and "peptide" are used interchangeably herein to refer to a polymer of amino acid residues. A polypeptide can be of natural (tissue-derived) origins, recombinant or natural expression from prokaryotic or eukaryotic cellular preparations, or produced chemically via synthetic methods. The terms apply to amino acid polymers in which one or more amino acid residue is an artificial chemical mimetic of a corresponding naturally occurring amino acid, as well as to naturally occurring amino acid polymers and non-naturally occurring amino acid polymer. Amino acid mimetics refers to chemical compounds that have a structure that is different from the general chemical structure of an amino acid, but that functions in a manner similar to a naturally occurring amino acid. Non-natural residues are well described in the scientific and patent literature: a few exemplary non-natural compositions useful as mimetics of natural amino acid residues and guidelines are described below. Mimetics of aromatic amino acids can be generated by replacing by, e.g. D- or L-naphylalanine: D- or L-phenylglycine: D- or L-2 thieneylalanine: D- or L-1, -2,3-, or 4-pyreneylalanine: D- or L-3 thieneylalanine: D- or L-(2-pyridinyl)-alanine: D- or L-(3-pyridinyl)-alanine: D- or L-(2-pyrazinyl)-alanine: D- or L-(4-isopropyl)-phenylglycine: D-(trifluoromethyl)-phenylglycine: D-(trifluoromethyl)-phenylalanine: D-p-fluoro-phenylalanine: D- or L-p-biphenylphenylalanine: K- or L-p-methoxy-biphenylphenylalanine: D- or L-2-indole (alkyl) alanines; and, D- or L-alkylainines, where alkyl can be substituted or unsubstituted methyl, ethyl, propyl, hexyl, butyl, pentyl, isopropyl, iso-butyl, sec-isotyl, iso-pentyl, or a non-acidic amino acids. Aromatic rings of a non-natural amino acid include, e.g. thiazolyl, thiophenyl, pyrazolyl, benzimidazolyl, naphthyl, furanyl, pyrrolyl, and pyridyl aromatic rings.

The term "antigen binding polypeptide" as used herein refers to antibodies, antibody fragments and other protein constructs which are capable of binding to an antigen.

The term "antibody" is used herein in the broadest sense to refer to molecules with an immunoglobulin-like domain (for example IgG, IgM, IgA, IgD or IgE) and includes monoclonal, recombinant, polyclonal, chimeric, human, humanised, multispecific antibodies, including bispecific antibodies, and heteroconjugate antibodies: a single variable domain (e.g. a domain antibody (DAB)), antigen binding antibody fragments, Fab, $F(ab')_2$, Fv, disulphide linked Fv, single chain Fv, disulphide-linked scFv, diabodies, TANDABS, etc. and modified versions of any of the foregoing (for a summary of alternative "antibody" formats see Holliger and Hudson, Nature Biotechnology, 2005, Vol 23, No. 9, 1126-1136). Alternative antibody formats are also contemplated and include alternative scaffolds in which the one or more CDRs of the antigen binding protein can be arranged onto a suitable non-immunoglobulin protein scaffold or skeleton, such as an affibody, a SpA scaffold, an LDL receptor class A domain, an avimer or an EGF domain.

The term, full, whole or intact antibody, used interchangeably herein, refers to a heterotetrameric glycoprotein with an approximate molecular weight of 150,000 daltons. An intact antibody is composed of two identical heavy chains (HCs) and two identical light chains (LCs) linked by covalent disulphide bonds. This $H_2L_2$ structure folds to form three functional domains comprising two antigen-binding fragments, known as 'Fab' fragments, and a 'Fc' crystallisable fragment. The Fab fragment is composed of the variable domain at the amino-terminus, variable heavy (VH) or variable light (VL), and the constant domain at the carboxyl terminus, CH1 (heavy) and CL (light). The Fc fragment is composed of two domains formed by dimerization of paired CH2 and CH3 regions. The Fc may elicit effector functions by binding to receptors on immune cells or by binding C1q, the first component of the classical complement pathway. The five classes of antibodies IgM, IgA, IgG, IgE and IgD are defined by distinct heavy chain amino acid sequences which are called μ, α, γ, ε and δ respectively, each heavy chain can pair with either a K or A light chain. The majority of antibodies in the serum belong to the IgG class, there are four isotypes of human IgG, IgG1, IgG2, IgG3 and IgG4, the sequences of which differ mainly in their hinge region.

As used herein "fragment," when used in reference to a protein or polypeptide, is a protein or polypeptide having an amino acid sequence that is the same as part but not all of the amino acid sequence of the entire naturally occurring protein/polypeptide. Fragments may be "free-standing" or comprised within a larger protein or polypeptide of which they form a part or region as a single continuous region in a single larger protein/polypeptide.

The term "single variable domain" refers to a folded polypeptide domain comprising sequences characteristic of antibody variable domains. It therefore includes complete antibody variable domains such as VH, VHH and VL and modified antibody variable domains, for example, in which one or more loops have been replaced by sequences which are not characteristic of antibody variable domains, or antibody variable domains which have been truncated or comprise N- or C-terminal extensions, as well as folded fragments of variable domains which retain at least the binding activity and specificity of the full-length domain. A single variable domain as defined herein is capable of binding an antigen or epitope independently of a different variable region or domain. A "domain antibody" or "DAB" may be considered the same as a human "single variable domain". A single variable domain may be a human single variable domain, but also includes single variable domains from other species such as rodent (for example, as disclosed in WO 00/29004), nurse shark and Camelid VHHs Camelid VHHs are immunoglobulin single variable domain polypeptides that are derived from species including camel, llama, alpaca, dromedary, and guanaco, which produce heavy chain only antibodies naturally devoid of light chains. Such VHH domains may be humanised according to standard techniques available in the art, and such domains are considered to be "single variable domains".

Figure 2:
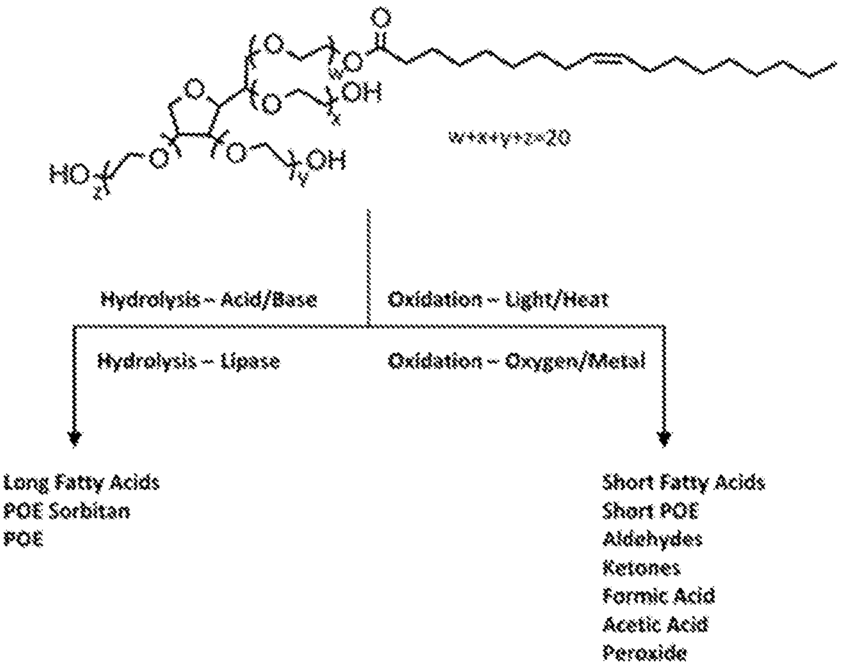
FIG. 2: shows the degradation products of the two most common types of degradation in polysorbates.

As used herein the term "polysorbate" refers to any one of (or all of) the common intact polysorbates selected from polysorbate 80 (PS80), polysorbate 60 (PS60), polysorbate 40 (PS40) and polysorbate 20 (PS20) and their degradation products. Intact polysorbate refers to polysorbate when present as a monoester. Degradation products of polysorbates that can be detected by the methods of the invention include: long chain fatty acids (e.g. palmitic acid, linoleic acid, oleic acids), polyoxyethylene (POE) groups including POE esters of fatty acids, and short chain fatty acids. FIG. 2: shows the degradation products of the two most common types of degradation in polysorbates.

Polysorbates are commonly used as non-ionic surfactants in both food and biopharmaceutical products. In biopharmaceutical products, they are used to prevent protein adsorption to surfaces, aggregation, and particle formation. However when the intact polysorbate degrades it is known to be problematic and for example degraded polysorbate products can cause irritation in injectibles of pharmaceutical products and also leads to excessive turbidity in the samples e.g. pharmaceutical samples. It is generally considered that between about 10 ppm to about 5000 ppm of intact polysorbate is a desirable amount in a pharmaceutical product.

Hence great interest lies in the development of analytical methods to monitor such polysorbates including the integrity of the polysorbates, and particularly polysorbate 80 (polyoxyethylene sorbitan mono-oleate or Tween™ 80) which is the most commonly used polysorbate. Commercially available PS80 is heterogenous, with the most common process related subspecies being polyoxyethylene (POE) groups, POE isosorbide mono-ester, and POE sorbitan/isosorbide di-, tri-, tetra-esters. FIG. 1: shows the last two steps of the synthetic route for polysorbate 80 (PS80).

However, the development of an analytical method to detect not only intact polysorbates such as PS80 and also PS60, PS40 and PS20 but also their degradation products has been challenging and there is a need for such a method and particularly a need for a method that can be applied to protein-containing biopharmaceutical formulations. Furthermore, the release of pharmaceutically acceptable protein material by agencies such as the FDA is dependent on the protein material containing defined levels of polysorbate including certain polysorbate products.

The present invention therefore provides a method that enables identification of such polysorbates, for example of intact polysorbate and/or degraded polysorbate products in pharmaceutical formulations such as biopharmaceutical formulations containing protein.

The invention also provides methods that enable measurement of polysorbate in biopharmaceutical formulations containing proteins or peptides. The term "measurement" of polysorbates as used herein refers to identification and also quantification of said polysorbates. The polysorbate measured can be intact and/or degraded polysorbate products. The methods provided herein are advantageous as they are accurate, can be performed in a similar time frame to traditional HPLC, and do not depend on use of derivatization or micelle encapsulation which can be problematic. Derivatization or micelle encapsulation may increase the complexity of sample preparation, depend on equilibrium kinetics which may negatively impact precision, and may employ additional components to the matrix that will negatively impact signal-to-noise ratio.

Hence the present invention provides in a first aspect a method of identifying polysorbate e.g. intact polysorbate and/or degraded polysorbate products in a sample containing protein e.g. an antibody such as a mAb sample, comprising subjecting said sample to the following steps: (i) precipitating the protein by exposing said sample to an organic protic polar solvent or an organic aprotic polar, (ii) separating the protein from the precipitated sample by centrifuging the precipitated sample to pellet the protein or peptide and obtaining a liquid supernatant, (iii) separating the polysorbates by subjecting the supernatant to chromatography, wherein the chromatography comprises applying the supernatant to a stationary phase column comprising an immobilised cyano group, and eluting the bound polysorbates using a mobile phase composition gradient, and (iv) detecting the separated polysorbates using a chromophore-lacking detector to identify polysorbate.

The steps of precipitating and separating combined with the elution allows separation of the polysorbate products in the sample e.g. intact and degraded polysorbate products, and the detection step allows the detection, identification and quantification of the polysorbate products e.g. intact and degraded polysorbate products such as intact PS80 and/or PS60 and/or PS40 and/or PS20 and their degradation products. In one embodiment the method of measuring intact polysorbate in a protein containing sample e.g. an antibody such as a mAb sample that is provided herein is a quantitative method which allows measurement of amounts of intact and/or degraded polysorbate products such as PS80 and/or PS60 and/or PS40 and/or PS20 present in said sample.

In an embodiment the methods of the invention can be used to monitor degradation of intact polysorbate in a sample such as a protein containing sample e.g. an antibody such as a mAb sample or a cell or a protein containing vector expressing a heterologous therapeutic gene, over time for example to assess stability of such protein containing samples.

The present invention also provides use of the methods to measure amounts of intact polysorbates in protein containing samples for example to measure amounts of intact PS80 and/or intact PS60 and/or intact PS40 and/or intact PS20 present in such samples.

In a second aspect the present invention provides a method for identification of a protein sample e.g. from a plurality of proteins, wherein said identified protein sample(s) contains from about 10 ppm to about 5000 ppm of intact polysorbate, and which comprises the following steps:

(a) measuring polysorbate in said protein samples, comprising the following steps:

(i) precipitating the protein by exposing said sample to an organic protic polar solvent or an organic aprotic polar solvent, (ii) separating the protein from the precipitated sample by centrifuging the precipitated sample to pellet the protein or peptide and obtaining a liquid supernatant, (iii) separating the polysorbates by subjecting the supernatant to chromatography, wherein the chromatography comprises applying the supernatant to a stationary phase column comprising an immobilised cyano group, and eluting the bound polysorbates using a mobile phase composition gradient, and (iv) detecting the separated polysorbates using a chromophore-lacking detector to identify polysorbate; (b) Identifying the protein sample(s) from (a) which have levels of intact polysorbate which are between about 10 ppm to about 5000 ppm; (c) Isolation and recovery of said protein(s) identified in step (b).

In one embodiment of the second aspect of the invention the intact polysorbate is PS80 and/or PS60 and/or PS40 and/or PS20.

Also provided is a protein obtained or obtainable by the method of the second aspect of the invention and also use of said protein in medicine e.g. in preparation of a pharmaceutical formulation for administration to a human subject.

The invention also provides a protein (e.g. antibody) obtainable or obtained from the method of the second aspect of the invention and which protein contains from about 10 ppm to about 4000 ppm or to about 3000 ppm or to about 2000 ppm or to about 800 ppm or to about 700 ppm of intact polysorbate present and also use of said protein in medicine e.g. in preparation of a pharmaceutical formulation for administration to a human subject.

In an embodiment when the protein is an antibody or a cell for use in cell therapy or a protein containing vector expressing a heterologous therapeutic gene the amount of intact polysorbate present in the protein is from about 10 ppm to about 700 ppm. The concentration of protein present in the sample and to which the methods of the invention can be applied can be from about 5 mg/ml to about 300 mg/ml, from about 5 to about 200 mg/ml, from about 5 to about 50 mg/ml, from about 5 to about 20 mg/ml, from about 5 to about 10 mg/ml, from about 10 to about 20 mg/ml, from about 15 or from about 20 mg/ml to about 50 mg/ml.

The methods of the invention can be applied to any natural or recombinant protein. The protein sample can for example comprise a therapeutic protein, prophylactic protein or a diagnostic protein. For example the methods can applied to samples comprising an antigen binding construct, such as an antibody or an antibody fragment e.g. a biologically functional fragment of an antibody, the methods can also be applied to vaccine compositions, cells or protein containing vectors expressing a heterologous therapeutic gene.

When the protein sample is an antibody it can be e.g. a monoclonal antibody (mAb) or a bispecific or multispecific antibody or a fragment thereof. The antibody can be chimeric, humanised or human. Where the protein is an antibody fragment this can be for example a Fab, $F(ab)_2$, Fv, disulphide linked Fv, single chain Fv, disulphide-linked scFv, diabodies, TANDABS™, CDRs of an antibody and modified versions of any of the foregoing.

The antibody fragment can also be a single variable domain (or dAb) such as a human VH or VL single variable domain or a single variable domain derived from non-human sources such as llama or Camelid, e.g. a Camelid VHH including a Nanobody™ (described for example in WO 94/04678 and WO 95/04079 inter alia). Use of the CDRs of any of these antibodies or single variable domains e.g. as part of a protein scaffold is also contemplated.

The protein samples for use in the methods of the invention can be in liquid or suspension form in an aqueous medium or they can be for example freeze dried and then reconstituted in an aqueous medium. The protein samples can further comprise additional diluents e.g. pharmaceutically acceptable diluents in addition to said proteins and water. Examples of such pharmaceutically acceptable diluents include solvents such as water, sodium chloride solution, sugars, buffers such as acetate, salts such as sodium chloride, and/or other excipients. In one embodiment the buffers are acetate and citrate.

The methods of the invention are particularly useful for detecting polysorbate e.g. intact polysorbate and degraded species of polysorbates e.g. PS80 and/or PS60 and/or PS40 and/or PS20 in protein containing liquid samples such as liquid biopharmaceutical formulations e.g. mAb formulations.

The methods of the invention can also be applied samples comprising oligonucleotides, engineered cells for cell therapy and also to gene therapy products such as engineered vectors (e.g. viral vectors) containing a therapeutic gene for administration to a human subject.

The methods of the invention can also be used for measuring polysorbate in samples comprising small molecules which are chemical entities (NCEs) and where such NCE samples do not comprise protein then protein precipitation can be omitted and amounts of organic protic polar solvent or an organic aprotic polar adjusted.

The methods of the invention can be performed across a wide range of pH as pH value is not critical to performance of the methods e.g. from about pH 5 to about pH 10, or about pH 6 to about pH 8. The protein samples analysed according to the methods of the present invention can have a pH between about pH 6.0 and about pH 8.0 for example a pH of about 7.4 to about 6.8.

Organic protic polar solvents for use in the protein precipitation step are well known in the art and the term as used herein refers to an organic solvent that contains labile protons and is ionisable. Examples of such solvents which can be used in the methods of the invention are well known to the skilled person and include for example methanol, ethanol, and isopropyl alcohol (IPA). For example when the protein is an antibody methanol, IPA or acetone can be used in the protein precipitation step.

Organic aprotic polar solvents for use in the protein precipitation step are also well known in the art and the term as used herein refers to an organic solvent that does not contain labile protons. Examples of such solvents which can be used in the methods of the invention are well known to the skilled person and include for example acetone, tetrahydrofuran (THF), and acetonitrile.

The methods can be performed across a wide range of concentration of solvents and when the methods are performed on samples comprising antibodies the volume/volume dilution can be from about 1 part sample to about 5, 9 or about 19 parts solvent.

The centrifugation step can be performed at a speed and time which is sufficient to obtain a protein pellet for example it can be performed at at least about 10,000 rpm for at least about 10 minutes.

The separation step can be performed using column chromatography methods, for example using a reverse phase medium or mixed mode retention chromatography. Such mixed mode chromatography involves the combined use of two or more retention mechanisms e.g. normal phase, cation exchange and anion exchange In an embodiment the separation step of the methods of the invention can be performed on a reverse phase chromatography column using methods known to one skilled in the art. and wherein said column comprise groups with carbon chains which are C3 or longer e.g. C4 up to about C18.

In one embodiment the column comprises an immobilised cyano group e.g. a reverse phase chromatography column comprising an immobilised cyano group on the stationary phase is used. A cyano group is well known in the art and is any chemical compound which contains the group-CN. Any cyano group can be used in the methods of the invention. Columns comprising CN groups which can usefully be used according to methods of the invention are Agilent Zorbax SB300—CN and include Agilent Zorbax SB300—CN, Phenomenex Luna CN, or Agilent InfinityLab Poroshell 120 EC-CN.

The column can be a silica bead column with for example a pore size of about 80 Angstroms or greater. In an embodiment the pore size is between about 120 to about 300 Angstroms in size. For example a pore size of about 300 Angstroms can be used. Examples of suitable silica columns include, Agilent Zorbax SB300—CN, Phenomenex CN, or Agilent Infinity Lab Poroshell 120 EC-CN). In one embodiment the column used is an Agilent Zorbax SB300—CN, 3.5 μm, 150×4.6 mm (obtainable from Agilent Co., Santa Clara, CA, USA). The column can be heated and for example the temperature of the column can be between about 20° C. and about 80° C., or about 40° C. to about 60° C. or about 50° C.

In an embodiment the elution step is performed using a gradient separated mobile phase and this can be for example a gradient separated mobile phase of A and B. In one embodiment a gradient separated mobile phase of A and B is employed wherein A is a 0.1% to about 10% mixture of acid or ammonium acetate in $H_2O$, the acid can be selected from Trifluoroacetic acid (TFA), formic acid, acetic acid, difluoroacetic acid and B can be methanol, isopropranol or acetonitrile. In an embodiment a gradient separated mobile phase of A and B is employed which is a mixture of 0.1% Trifluoroacetic acid (TFA) in $H_2O$ and B is methanol or acetonitrile. The gradient separated mobile phase of A and B can be performed as detailed below in Table 1.

TABLE 1

| Time (min) | % A | % B |
|---|---|---|
| 0 | 100 | 0 |
| 1 | 100 | 0 |
| 3 | 50 | 50 |
| 8 | 50 | 50 |
| 27 | 5 | 95 |
| 30 | 5 | 95 |
| 30.1 | 100 | 0 |
| 40 | 100 | 0 |

The detector used in the methods of the invention is a chromophore-lacking detector and such a detector is one which functions when the sample for detection lacks a chromophore.

In an embodiment the detector used in the methods of the invention can be an evaporative light scattering detector or mass spectrometry can be used for detection.

In another embodiment a charged aerosol detector (CAD) is used as the detector in the methods of the invention, this is a detector that is used in conjunction for example with high performance liquid chromatography (HPLC) and works by charging non-volatile and semi-volatile analytes with nitrogen gas that has been charged by a high-voltage corona wire. The charged analyte particles then pass through an ion trap which removes high-mobility species (i.e., solvent) and continue traveling to a collector where they are measured by a sensitive electrometer. Examples of CADs that can be used include the Corona Veo (obtainable from Thermo Waltham, MA, USA), Corona Veo RS (obtainable from Thermo Waltham, MA, USA), and Vanquish (obtainable from Waltham, MA, USA), Corona Ultra and Ultra RS (obtainable from Thermo Waltham, MA, USA), Corona Plus (obtainable from Thermo Waltham, MA, USA).

One of the features that a CAD offers is an ability to measure intact species by charging the surface of the analyte, unlike mass spectrometry which creates charged fragments. Additionally, for analytes with similar surface area and density, the response is similar. Lastly, if a very volatile eluent is used, CAD methods can also be very sensitive (sub-nanogram).

While a CAD is easily operated, there are additional considerations in the development of standard HPLC-UV/Vis analytical methods. These include: (1) choosing a column that does not shed: (2) utilization of high purity solvents in mobile phases for low, reproducible baselines; and (3) cleaning glassware and plastics, due to the larger likelihood of interference from contaminants. It is important to achieve specificity when employing a CAD as there is no way to discern peak purity as when employing diode array or mass spectrometer (MS) detection. It should also be noted that if specificity is not achieved, the observed signal is not simply the sum of responses as in UV-Vis spectrophotometry, and differences in response are often complicated by differences in charge, surface area, density, and volatility of the analyte with respect to the components of the mobile phase. For these reasons, the CAD is well suited as a detector for the analysis of PS80.

In an embodiment the charged aerosol detector (CAD) used in the methods described herein is the Corona Veo RS (obtainable from Thermo, Waltham, MA, USA).

The detection step performed using the CAD results in obtaining a chromatogram in which the baseline is obtained using a chosen blank solution(s) and which contains a peak area for the intact polysorbate, for the degradation products as well as for the protein and excipients in the sample. Assessment of the peak area using an area under the curve calculation allows the quantification of polysorbates such as PS80, and/or PS60, and/or PS40 and/or PS20 and their degradation products. In an embodiment the method allows identification of PS80 for example intact and degraded PS80.

When we refer to separation using the methods of the invention what is meant is that the intact polysorbate peak (i.e. the monoester) must be resolved from the oleic acid peak. The resolution between the oleic acid peak and intact polysorbate monoster peak is 1.5 or greater. Other peaks need to simply be distinguishable from one another. Additionally in an embodiment there is a specificity requirement that is that there are no interfering peaks at the retention time of the intact polysorbate (i.e. monoester) greater than about 3% by area. In an embodiment the present invention provides a method of identifying polysorbate in a sample containing protein (e.g. an antibody sample) comprising:

(i) precipitating the protein by exposing said sample to methanol or IPA, (ii) separating the protein from the precipitated sample by centrifuging the precipitated sample to pellet the protein or peptide and obtaining a liquid supernatant, (iii) separating the polysorbates by subjecting the supernatant to reverse phase HPLC on a silica column with pore size of about 300 Angstroms and which comprises an immobilised cyano group and eluting using a mobile phase composition gradient consisting of A and B wherein A is a mixture of 0.1% Trifluoroacetic acid (TFA) in $H_2O$ and B is methanol or acetonitrile, (iv) detecting the separated polysorbates using a charged aerosol detector (CAD) to identify the polysorbate products.

EXAMPLES

The present invention is further described with reference to the following examples. These examples are merely to illustrate various aspects of the present invention and are not intended as limitations of this invention Example 1: Comparison of measuring PS80 and its subspecies present in mAb drug product via either (i) a novel HPLC-CAD analysis according to the method of the invention, with the ability to quantify the PS80 mono-ester, and (ii) a modified HPLC method using evaporative light scattering detection—HPLC-ELSD method.

Reagents and methods used were as follows:

The multi-compendial J.T. Baker PS80 was purchased from Fisher Scientific (Atlanta, GA, USA, 02-003-654). Two sources of PS80 were purchased from Sigma-Aldrich (St. Louis, MO, USA): (1) PS80 stored in a natural-colored plastic container (Part #P1754-25ML), and (2) PS80 stored in an amber, glass container (Part #59925-100G). Super refined PS80 was purchased from Croda Health Care (Edison, NJ, USA, SR48833). All-oleate ChP-compliant PS80 was purchased from NOF (White Plains, NY, USA), non-GMP PS80, POLO80 (HX2) 19B803364). Polysorbate 60 was purchased from USP Reference Standard (Rockville, MD, USA, 154794). Polysorbate 40 was purchased from Fisher Scientific (Atlanta, GA, USA, AC334142500). Oleic acid was purchased from Sigma-Aldrich (St. Louis, MO, USA, 75090-5ML). Linoleic acid was purchased from Fisher Scientific (Atlanta, GA, USA, AC215040250). Palmitic acid was purchased from MP Biomedicals (Santa Ana, CA, USA, 100905-10G). Palmitoleic acid was purchased from Sigma-Aldrich (St. Louis, MO, USA, 76169). Chromatographic (LC-MS or GC) grade methanol was purchased from Fisher Scientific (Atlanta, GA, USA, A456-4) or VWR (Honeywell/Burdick and Jackson, GC grade, ≥99.9% pure, BJGC 230-4). A Milli-Q water purification system (Millipore Corporation, Burlington, MA, USA) was used to generate ultrapure water (MilliQ water). Trifluoroacetic acid (TFA) was purchased from Sigma-Aldrich (St. Louis, MO, USA, 91707-10×1 mL). Other precipitating solvents (isopropanol, acetone, tetrahydrofuran (THF)) were chromatographic grade and purchased from Sigma-Aldrich. For the HPLC-ELSD method, HPLC-grade methanol (646377-4L) and acetonitrile (439134-4L) were purchased from Sigma-Aldrich (St. Louis, MO, USA). Honeywell Fluka formic acid (94318-250ML) was purchase from Fisher Scientific (Atlanta, GA, USA, AC334142500).

Instrumentation and analytical conditions used were as follows:

Protein Precipitation and PS80 Extraction:

For the Novel HPLC-CAD analytical method this was performed as follows:

To remove the protein [i.e. mAb drug product] prior to injection, the protein was precipitated via a precipitating solvent (methanol, isopropanol, and/or acetone). Additionally, precipitation was employed to disrupt any potential protein-PS80 interactions and inhibit any degradation occurring by lipases or esterases. Filtration was not a viable option due to the removal of some polysorbate species. Thus, 900 μL of precipitating solvent were added to 100 μL of sample in a pre-rinsed (with methanol or precipitating solvent) 1.5 mL Eppendorf safe-lock tube (Hauppauge, NY, USA, 022363204). The sample preparation was then mixed briefly (~5 sec) by vortexing, and centrifuged at 14,000 rpm for 10 min. The PS80 species and fatty acids remained soluble in the supernatant. A minimum of 60 μL of the supernatant were transferred to HPLC vials equipped with a 300 μL insert.

The 1,000 ppm PS80 stock standard solution was prepared by weighing 100±10 mg of multi-compendial J.T. Baker PS80 into a 100 mL Class A volumetric flask and diluting to volume with methanol. The 20 ppm PS80 working standard solution was prepared by mixing 100 μL of MilliQ water, 20 μL of 1,000 ppm PS80 stock standard solution, and 880 μL of methanol in a pre-rinsed (with precipitating solvent) 1.5 mL Eppendorf tube by vortexing. Thus, the final diluent composition (90% precipitating solvent: 10% MilliQ $H_2O$/aqueous) for the standards was the same as that of the samples. The PS60, PS40, and PS20 solutions were prepared in the same manner.

A resolution check solution was prepared containing 20 ppm PS80 and 5 ppm oleic acid stock standard solution. A sensitivity solution was prepared by mixing 898 μL of organic solvent, 100 μL of water, and 2 μL of the 1,000 ppm PS80 stock standard solution. The mAb formulation buffer was prepared in bulk, aliquoted, and stored at −70° C. until the day of analysis. A 20 ppm PS80 formulation buffer preparation was made by diluting with LC-MS or GC grade methanol. Centrifugation steps were not required for sample preparations lacking protein.

For the thermally stressed samples, multiple vials of the mAb/protein-containing formulation were incubated at −70, 5, 25, and 40° C. for 3 weeks and a vial was removed from the oven at each time point (initial, 1, 2, 3, 4, 7 14 and 21 d) and frozen at −70° C. until the time of analysis.

For the Modified HPLC-ELSD analytical method this was performed as follows:

Due to a suspected PS80-protein interaction and to stop any enzymatic degradation, the protein was precipitated with methanol, instead of diluting with water. To precipitate the protein and extract the PS80, 800 μL of organic solvent was added to 200 μL of sample in a 1.5 mL microcentrifuge tubes and vortexed to mix. After mixing, the samples were centrifuged at 10,000 rpm for 30 minutes at 5° C. After centrifugation, 200 μL of supernatant were transferred to HPLC vials equipped with a 300 μL insert.

Figure 9:
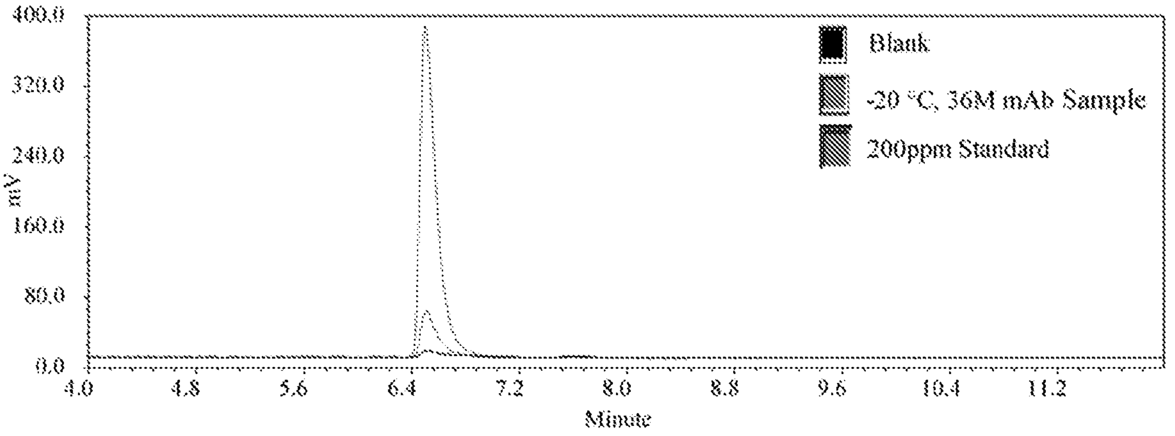
FIG. 9: shows overlay of chromatograms (200 ppm standard solution (multi-compendial J.T. Baker PS80), mAb sample with degraded PS80, and blank solution.

Quantification of the PS80 content in the samples was achieved through the preparation of a calibration curve. Due to the nature of the HPLC-ELSD detector, the matrix of the standard curve must be representative of the samples. To achieve a representative matrix, 500 mg of multi-compendial J.T. baker PS80 was weighed into a 50.0-mL low actinic Class A volumetric flask and diluted to volume with HPLC grade methanol to prepare a 10,000 ppm PS80 stock solution. Then, 0.5 mL of the 10,000 ppm PS80 stock solution was then added to a 10.0-mL volumetric flask and brought to volume with HPLC grade methanol to prepare a 500 ppm stock solution. The 500 ppm stock solution was used to prepare calibration standards in methanol/water solution (80:20 v/v) with expected PS80 concentrations of 10, 25, 50, 100, 150, 200, and 250 ppm. A 20 ppm PS80 preparation was made by diluting with HPLC grade methanol. Centrifugation steps were not performed for preparations lacking protein. A sample chromatogram is provided in FIG. 9. In summary FIG. 9 shows overlay of chromatograms (200 ppm standard solution (multi-compendial J.T. Baker PS80), mAb sample with degraded PS80, and blank solution) collected with the modified HPLC-ELSD method. In FIG. 9 the 200 ppm standard has the largest peak and the −20 sample has the intermediate smaller peak.

Novel HPLC-CAD Method:

An Agilent HPLC 1260 system (Santa Clara, CA, USA) included a binary solvent manager, a sample manager set at 23° C., a column oven set at 50° C. and a charge aerosol detector (CAD) Veo RS (Thermo, Waltham, MA, USA). The CAD was connected directly to the analytical column via 80 cm of tubing (Agilent, 01078-87305), which was connected directly to the 3 µL peltier with 180 mm of tubing (Agilent, G1313-87305). The HPLC column heater was connected to the HPLC autosampler via standard tubing and both the UV-VIS and column switching valve were bypassed.

The analytical column was a Zorbax SB300—CN (150 mm×4.6 mm, 3.5 µm 300 Å, 863973-905) from Agilent Technologies (Wilmington, DE, USA). Volatile mobile phases (MP) comprised of 0.1% v/v TFA in MilliQ water (MP A) and 100% LC-MS or GC grade methanol (MP B) were employed. Additionally, the mobile phase was pre-screened for cleanliness by flowing at 1.2 mL/min at 35% MP A: 65% MP B and ensuring that the CAD had a baseline level under 10 mV with the parameters listed above. Separation of the PS80 subspecies was achieved by gradient elution (0.1% TFA in MilliQ water was: 0 min.-100%; 1 min.-100%; 3 min.-50%; 8 min.-50%; 27 min.-5%; 30 min.-5%; and 30.1 min.-100%) at a flow rate of 1.2 mL/min. The total run time of the method was 40 min. The injection volume was 30.0 µL. A Thermo Veo RS CAD was operated with the following settings: evaporation temperature, 60° C.; power function, 1.00; output offset, 0%; filter, 5.0 sec; range 100 pA. An in-house nitrogen supply was used. The CAD analog signal was converted to a digital signal through the use of an e-SAT/IN module (Waters, Milford, MA, USA, 668000230).

Modified HPLC-ELSD Method:

This method was a modified method from those of Hewitt and Koppolu. An Agilent HPLC 1100 system (Santa Clara, CA, USA) included a binary solvent manager, a sample manager set at 25° C., a column oven set at 30° C. and a 1260 Infinity G4260B evaporative light scattering detector (ELSD, Agilent Technologies, Wilmington, DE, USA). The ELSD was connected directly to the analytical column, which was connected directly to the 3 µL peltier. The HPLC column heater was connected to the HPLC autosampler via standard tubing and both the UV-VIS and column switching valve were bypassed.

The analytical column was an Oasis® MAX (20 mm×2.1 mm, 30 µm 80 Å, Part #186002052) from Waters Corporation (Milford, MA, USA). Volatile mobile phases comprised of 2% v/v formic acid in MilliQ water and 2% v/v formic acid in isopropanol were employed. Separation was achieved by gradient elution (2% formic acid in MilliQ water was: 0 min.-90%; 1 min.-80%; 3.4 min.-80%; 3.5 min-0%; 4.5 min-0%; 4.6 min-90%; and 10 min-90%) at a flow rate of 1.0 mL/min with the flow diverted from the ELSD the first 4 min of the run. The injection volume was 50.0 µL. An Agilent 1260 Infinity G4260B ELSD was operated with the following settings: LED, 10; gain (PMT), 2; smooth (Smth), 1; data output, 80 Hz; evaporation temperature, 80° C.; nebulizer temperature, 50° C.; gas flow (SLM), 1. An in-house nitrogen supply was used. The CAD analog signal was converted to a digital signal through the use of an e-SAT/IN module (Waters, Milford, MA, USA, 668000230).

For the Novel HPLC-CAD analytical method data analysis, integration and calculations were performed as follows:

The mean of the PS80 mono-ester concentration of triplicate preparations was reported. To quantify the total-esters (mono-ester and multi-esters) for comparison to the modified HPLC-ELSD method, a calibration curve was made for total-esters by grouping the areas of the PS80 mono-ester and multi-esters in the linearity preparations. Thus, the total-esters area in the HPLC-CAD method is analogous to the single peak in the modified HPLC-ELSD method: the POE groups are not included in the single peak because they elute when the that valve switch is diverted to waste during the first 4 min of each injection.

Arrhenius kinetic modeling was employed to assess the rate of PS80 degradation and to estimate the stability or activation energy ($E_a$). It was assumed that the hydrolytic degradation of the PS80 mono-ester was pseudo first-order, as previously described. The rate constants were determined from the slope of the plot of the natural log of the concentration versus time, with the assumption that there was no significant effect due to a change in dynamic viscosity. For all linear plots, the relative error analysis of the slope was carried out as described previously:

$$\text{Slope error} = \sqrt{\frac{n}{n\sum x_i^2 - \left(\sum x_i\right)^2}} * \sqrt{\frac{\sum (y_i - ax_i - b)^2}{n-2}} \qquad \text{Equation 1}$$

where n is the number of data points, a is the slope and b is the y-intercept.

For the modified HPLC-ELSD analytical method data analysis, integration and calculations were performed using Empower 3 such that batch data processing was permitted to obtain retention time, peak area, and other chromatographic figures of merit. Similarly, for the novel HPLC-CAD method data analysis, integration, and calculations were performed using Empower 3 such that batch processing data processing was permitted to obtain retention time, peak area, resolution, S/N, and other chromatographic figures of merit.

Results

The novel HPLC-CAD method described above was found to accurately and precisely quantify the PS80 mono-ester and qualitatively/semi-quantitatively monitors four other groups of subspecies. For simplicity, we chose a concentration range that was linear even though the CAD response is nonlinear. The calibration curve can also be linearized by applying a power-function algorithm; however, without baseline reproducibility, such algorithms may not always hold true.

Figure 3:
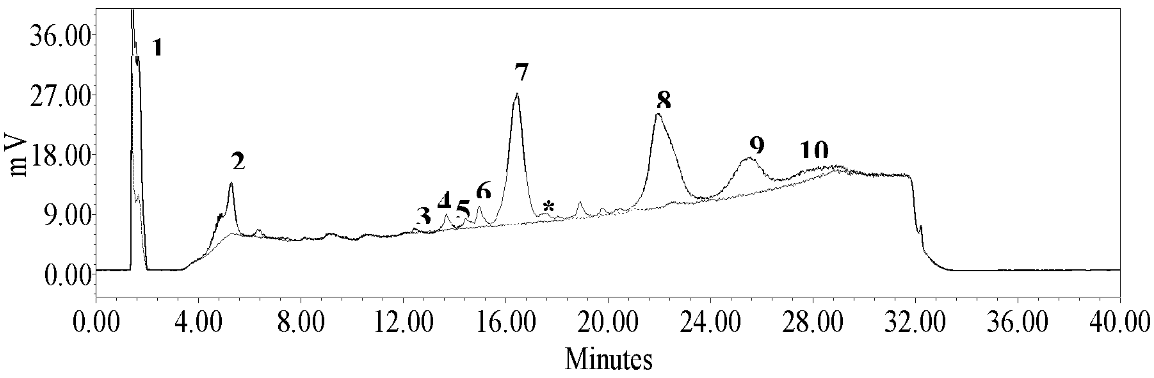
FIG. 3: shows a chromatogram obtained using the HPLC-CAD method which quantifies PS80 mono-ester and qualitatively/semi-quantitatively monitors four other groups of subspecies.

Matrix interference was evaluated by assessing the recovery of spiked PS80 in: (1) PS80-free IgG drug product; and (2) a mAb sample with completely degraded (<limit of quantitation (LOQ)) PS80 mono-ester (see Table 2 and discussion below). The degraded samples contained a protein in an aqueous buffer containing trehalose, methionine, arginine, histidine, mM EDTA, and PS80. Other samples contained a protein in an aqueous buffer containing trehalose, citrate, EDTA, and PS80. To assess specificity in degraded samples, fatty acids (linoleic acid, palmitic acid, oleic acid, and palmitoleic acid) were also spiked into a 20 ppm PS80 working standard solution at a concentration of 5 ppm (see FIG. 3). In summary FIG. 3 shows a chromatogram obtained using the HPLC-CAD method detailed which quantifies PS80 mono-ester and qualitatively/semi-quantitatively monitors four other groups of subspecies. It shows an overlay of blank (dashed) and 20 ppm PS80 (multi-compendial J.T. Baker) standard solution spiked with 10 ppm fatty acids (solid). Peaks: 1=non-retained formulation buffer components (trehalose, amino acids, EDTA, salt impurities in solvents, and/or sample residuals); 2=POE groups; 3=Palmitoleic acid; 4=Linoleic acid; 5=Palmitic acid; 6=Oleic acid; 7=PS80 mono-ester (sorbitan and isosorbide); 8=Di-esters; 9=Tri-esters; 10=Tetra-esters; * if present, a contaminant from the Eppendorf tubes. The identification of the PS80 peaks is assumed to be in agreement with previously reported LC-MS results [17, 30] and by the expected elution order of the analytes based on their relative hydrophobicities.

Method qualification with mAb drug product was completed.

It was comprised of precision, linearity, accuracy, specificity, and LOQ (Table 2). Using the CAD response for each injection, the mean concentration, standard deviation, and relative standard deviation were calculated. Precision was assessed through analysis of the mean of triplicate preparations on two to three occasions. Precision was also assessed using formulation buffer (or assay control) through a repeatability analysis of duplicate injections on five assay occasions between two analysts. Intermediate precision was determined by one analyst performing two independent assay occasions on one system and a second analyst performing three independent assay occasions on a second system.

TABLE 2

Accuracy, repeatability, intermediate precision, and linearity of PS80 mono-ester in formulation buffer and a mAb formulation.

| | Mean $R^2$ | Recovery (%) | RSD (%) |
|---|---|---|---|
| Repeatability—Formulation Buffer 1 (n = 5) | | | 0.7 |
| Repeatability—Formulation Buffer 2 (n = 5) | | | 1.3 |
| Repeatability—mAb Sample (n = 5) | | | 2.2 |
| Intermediate Precision—Formulation Buffer 1 (n = 5) | | | 4.7 |
| Intermediate Precision—Formulation Buffer 2 (n = 5) | | | 5.5 |
| Intermediate Precision—mAb Sample (n = 5) | | | 6.5 |
| Linearity (n = 5) | 0.9992 | | |
| Accuracy (n = 5, Recovery of Spiked Samples) | | 101 | 1.7 |

The mAb drug product was tested in triplicate and results statistically analyzed to determine a mean concentration, standard deviation, and relative standard deviation.

The linearity was assessed via replication of five independent assay occasions with two analysts. The coefficient of determination ($R^2$) of each curve was determined by linear regression. Accuracy was determined using a spiked recovery approach. Two analysts introduced 20 ppm PS80 to a sample without PS80 in the formulation in triplicate on five assay occasions. This preparation was also used to confirm specificity. Specificity was also assessed by the resolution of the PS80 mono-ester and oleic acid peaks in the resolution check solution and by ensuring that no interfering peaks were within the elution window (+0.5 min) of PS80 mono-ester in 90% organic solvent/10% water blank injections. Peak specificity was demonstrated as no peak greater than 2% area with respect to the area of the standard was observed, since CADs are universal detectors and sometimes pick up small traces of contaminants. The signal-to-noise ratio (S/N) was estimated to be ≥10 for a 2 ppm PS80 solution.

TABLE 3

Weight-adjusted peak areas of PS80 mono-ester.

| PS80 Source | Amount (mg) | Adjusted* Peak Area (μV * sec) | Normalized Area % |
|---|---|---|---|
| All-oleate ChP-compliant | 94.8 | 755454 | 81.1 |
| Croda Super-Refined | 105.9 | 931421 | 100 |
| Sigma-Aldrich—Natural colored plastic container | 97.9 | 741002 | 79.6 |
| Sigma-Aldrich—Amber, glass container | 101.7 | 822437 | 88.3 |
| Multi-compendial J.T. Baker | 106.3 | 923193 | 99.1 |

*The peak areas of the 20 ppm PS80 solutions were weight-adjusted (weight-adjusted peak area = measured peak area * (actual weight (mg))/100 mg) to an exact mass of 100.0 mg for direct comparison.

Figure 4:
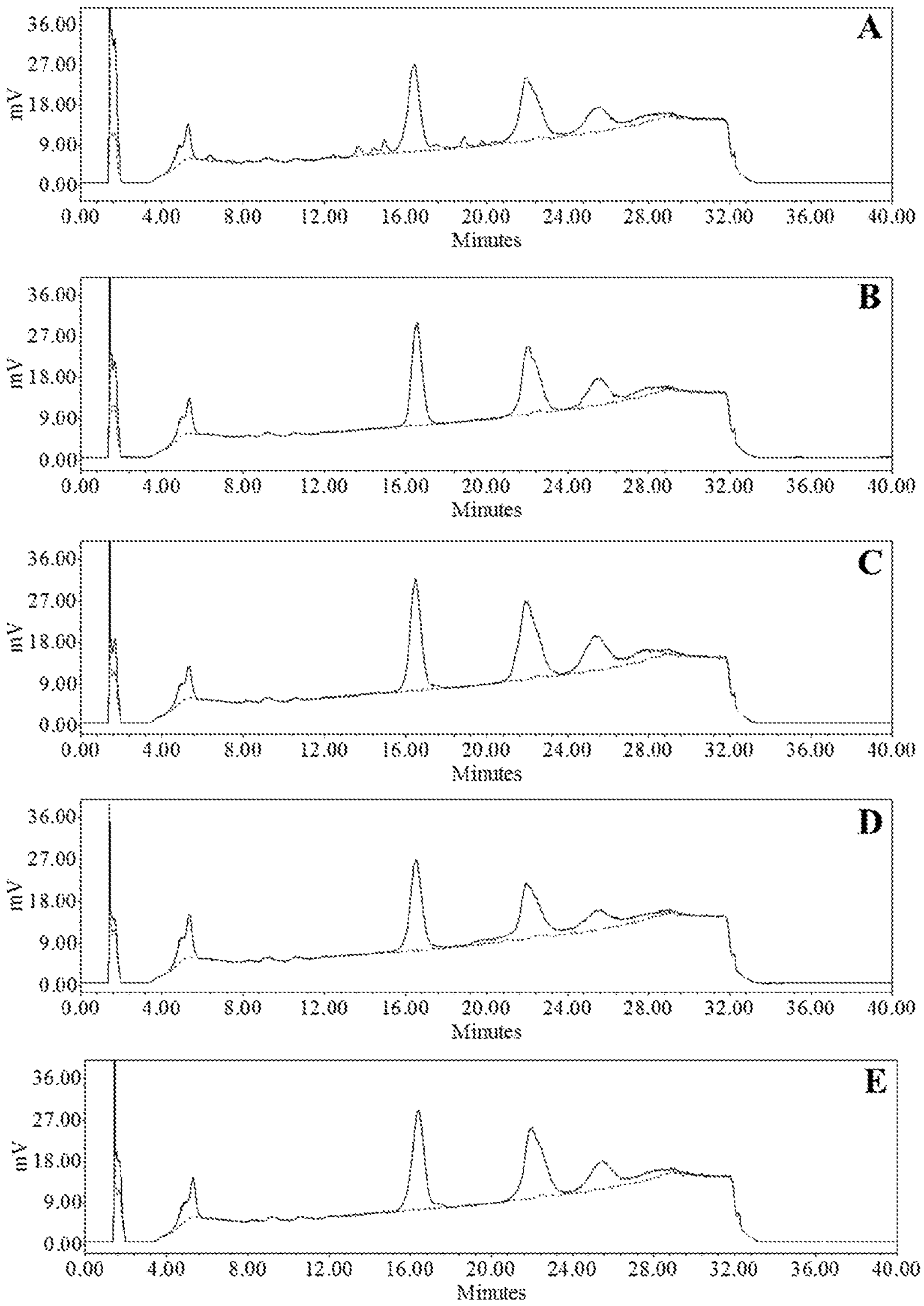
FIG. 4: shows Chromatograms for various sources of PS80s (solid) and blank (dotted).

Various sources and types of PS80 were tested with this method (Table 3). As demonstrated by FIG. 4, the chromatograms of each PS80 source were visually comparable. In summary FIG. 4 shows chromatograms for various sources of PS80's (solid) and blank (dotted): (A) all-oleate ChP-compliant PS80; (B) Sigma-Aldrich PS80 stored in an amber, glass container; (C) Croda super-refined PS80; (D) Sigma-Aldrich PS80 stored in a natural-colored, plastic container; and (E) multi-compendial J.T. Baker PS80.

Assuming equal PS80 mono-ester in all-oleate PS80 and multi-compendial J.T. Baker PS80, the peak area of all-oleate PS80 would be higher as a consequence of slightly larger molecular weight. The inconsistency of the synthetic routes for polysorbates has resulted in an observation of some variability in subspecies between batches. Physicochemical properties have been demonstrated to vary from batch to batch. As demonstrated by alternate storage containers of Sigma-Aldrich PS80, it is recommended that PS80 standard solutions be prepared with material that is from the same source and lot as the PS80 used in the biopharmaceutical formulation.

Figure 5:
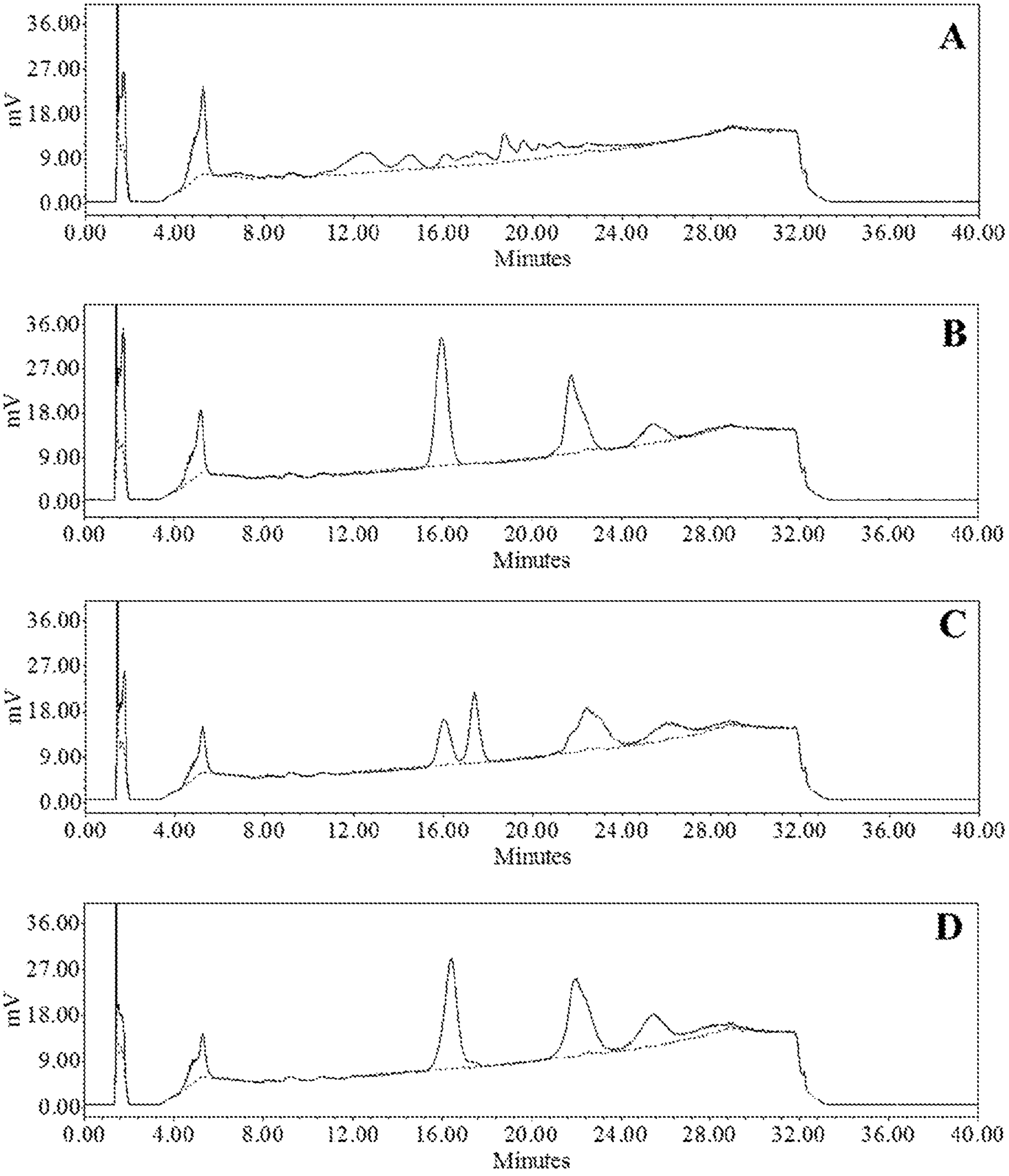
FIG. 5: shows chromatograms for various polysorbates (solid line) and blank (dotted line).

Polysorbate 40 (PS40, polyoxyethylene (20) sorbitan mono-palmitate) and polysorbate 60 (PS60, polyoxyethylene (20) sorbitan mono-stearate) were also assessed (FIG. 5), and each chromatographic profile resolved the mono-ester from the multi-esters. In summary FIG. 5 shows chromatograms for various polysorbates (solid line) and blank (dotted line): (A) Polysorbate 20 (polyoxyethylene (20) sorbitan monolaurate); (B) Polysorbate 40 (PS40, polyoxyethylene (20) sorbitan mono-palmitate); (C) polysorbate 60 (PS60, polyoxyethylene (20) sorbitan mono-stearate); and (D) Polysorbate 80 (polyoxyethylene (20) sorbitan monooleate). Each chromatographic profile resolved the mono-ester from the multi-esters. PS60 appears to contain two major mono-ester forms or a significant amount of POE isosorbide mono-ester; further investigation via mass spectrometry may be needed to discern the identity of these peaks. Multi-compendial polysorbate 20 (PS20, polyoxyethylene (20) sorbitan mono-laurate) was also included but yielded a complex chromatogram (SM FIG. 7). A complex chromatogram with PS20 has been previously reported and a simpler chromatogram was achieved by the use of all-laurate PS20. PS60 appears to contain two major mono-ester forms or a significant amount of POE isosorbide mono-ester; further investigation via mass spectrometry may be needed to discern the identity of these peaks.

Thus, this method has useful application to PS20, PS40, and PS60.

Figure 6:
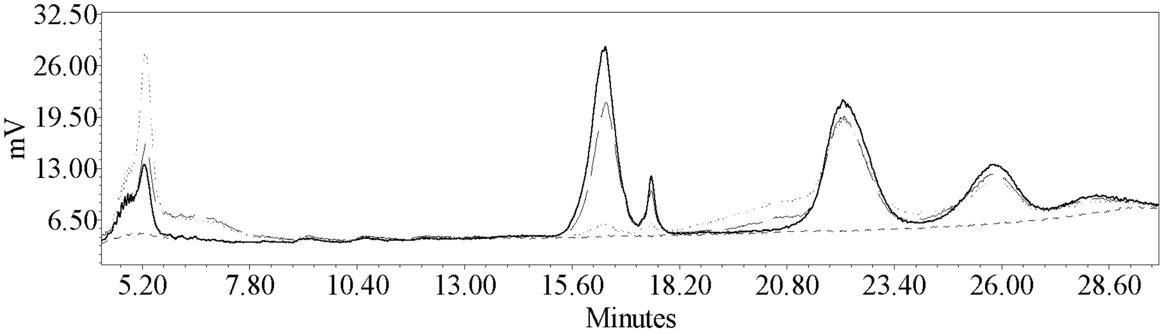
FIG. 6: shows a chromatographic profile obtained using the HPLC-CAD method of the PS80 mono-ester.

To assess method accuracy and specificity in terms of the PS80 mono-ester, a sample with complete mono-ester degradation was spiked and analyzed using a mAb. PS80 mono-ester degradation was achieved via incubation of the sample at 5° C. for 36 months (FIG. 6). In summary FIG. 6 shows a chromatographic profile obtained using the HPLC-CAD method of the PS80 mono-ester, a sample with complete mono-ester degradation which was spiked and analyzed using a mAb. PS80 mono-ester degradation was achieved via incubation of the sample at 5° C. for 36 months. The figure shows overlay of chromatograms collected via the novel CAD method demonstrating peak broadening of the multi-esters due to oxidative degradation in mAb product stored at 5 and −20° C. for 36 months. Additionally, nearly complete degradation of the mono-ester corresponds with an increase in POE groups. The standard was J.T. Baker, multi-compendial PS80. The peak at 17.5 min is a variable contaminant from Eppendorf tubes that were not pre-rinsed. The degraded sample was analyzed, confirming the absence of a quantifiable amount of PS80 mono-ester (<LOQ). As expected, the degradation of PS80 mono-ester produced a marked increase of POE groups. To determine if the subsequent degradation interfered with mono-ester quantification, a spiked recovery approach was employed. A degraded sample preparation was spiked with 20 ppm PS80, which correlates with a 200 ppm PS80 sample concentration. PS80 mono-ester was recovered at a value of 93%, confirming that significant increases in degradation products do not adversely impact the detection of mono-ester. Additionally, the multi-ester peaks decreased slightly and demonstrated peak broadening. This can most likely be attributed to the degradation and reformation of oxidized degradants with slightly different hydrophobicities and/or size after participating in radically-induced degradation.

Comparison of the ELSD and CAD Methods:

A series of samples were prepared and tested using both methods. The samples were formulation buffer and mAb product stored at 5 and −20° C. for 36 months, with or without one freeze-thaw (FT) cycle. Since the modified ELSD method incorporates a diversion during the first 4 min, POE groups and proteins purportedly do not pass through the detector, as inferred from previously reported method. Direct comparison of the total-esters in the two methods is summarized in Table 4 and demonstrated good agreement.

TABLE 4

Comparison of the modified HPLC-ELSD method and the novel CAD method with a 36M at 5° C. mAb sample. The percent agreement was calculated as, % Agreement = [C2/C1] * 100%, where C1 and C2 are the PS80 total-ester concentration determined by the HPLC-HPLC-ELSD and HPLC-CAD methods, respectively.

| Sample | [Mean PS80 Total-ester] (ppm)[1] | [Mean PS80 Mono-ester] (ppm)[2] | [Mean PS80 Total-ester] (ppm)[2] | % Agreement |
|---|---|---|---|---|
| 36M at −20° C. | 134 | 144 | 138 | 103 |
| 36M at −20° C./ 1 FT cycle | 127 | 142 | 143 | 113 |
| 36M at 5° C. | 95 | <20 | 99 | 104 |
| Formulation buffer | 150 | 152 | 152 | 101 |

[1]Modified HPLC-ELSD method;
[2]Novel HPLC-CAD method.

This method has been verified with IgG1, IgG2, and IgG4 mAbs (Table 5). During this investigation it was found that some precipitating solvents (e.g., acetone, THF) had low or poor recovery of the PS80 mono-ester or subspecies in the formulation buffer (data not shown).

TABLE 5

Various mAb formulations that the novel CAD method has been verified with.

| Asset | Precipitating Solvent |
|---|---|
| mAb1 | Methanol |
| mAb2 | Methanol |
| mAb3 | Methanol |
| mAb4 | Methanol |
| mAb5 | Methanol |
| mAb6 | Methanol |
| mAb7 | Methanol |
| mAb8 | Methanol |
| mAb9 | Isopropanol |
| mAb10 | Isopropanol |
| mAb11 | Isopropanol |

Figure 7:
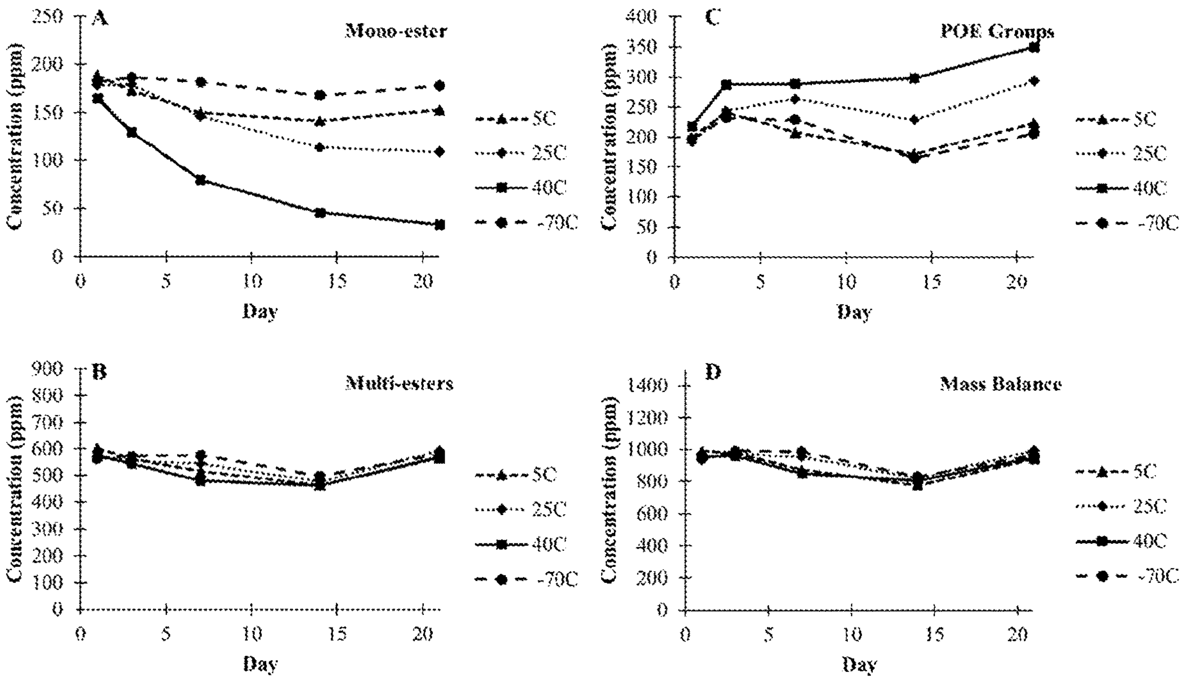
FIG. 7: shows Kinetics of PS80 degradation in samples at 5, 25, 40, or −70° C. up to 21 days.
Figure 8:
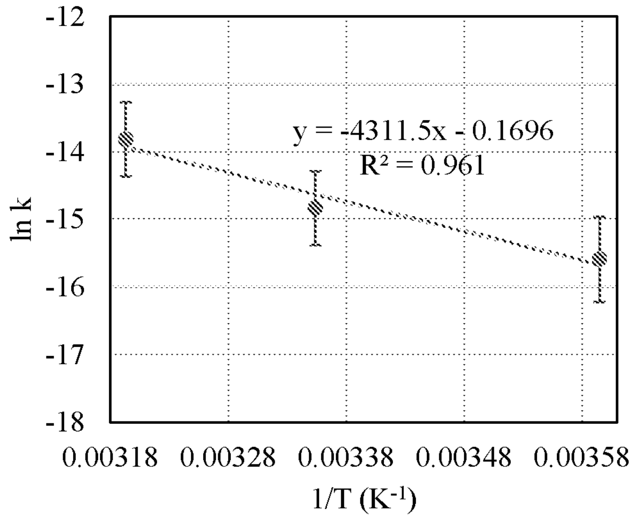
FIG. 8: shows Arrhenius plot of rate constants (at 5, 25 and 40° C.) for the degradation of the PS80 mono-ester.

Example 2: PS80 Kinetic study: Concentration-time data were obtained by quantifying the amount of PS80 mono-ester and subspecies for each time point (initial, 1, 2, 4, 7, 14, and 21 d) with the novel HPLC-CAD method (FIG. 7). In summary FIG. 7 shows Kinetics of PS80 degradation in samples at 5, 25, 40, or −70° C. up to 21 days. (A) Mono-ester, (B) Multi-esters (di-, tri-, and tetra-esters), (C) POE Groups, and (D) total mass balance were quantified. Here, the PS80 mono-ester peak was truly quantitative while the subspecies were semi-quantitative. Concentration-time data were obtained by quantifying the amount of PS80 mono-ester and subspecies for each time point (initial, 1, 2, 4, 7, 14, and 21 d) with the novel HPLC-CAD method. For the truly quantifiable PS80 mono-ester, an Arrhenius plot was compiled for the degradation of the PS80 mono-ester with the rate constants for the 5, 25, and 40° C. data, resulting in an activation energy for the PS80 mono-ester of 35.8±7.2 kJ/mol; the linear least square fitting resulted in $y=4311.5x-0.1696$, with an $R^2=0.961$. (FIG. 8). The observed activation energy is similar to previous published observations for PS80 hydrolysis as Kishore reports an activation energy of ~35 kJ/mol for the degradation of the first ~30% of PS80. However, the employed analytical method did not have the specificity to distinguish the mono- and multi-ester forms. In our study, since the degradation was mostly likely hydrolytic degradation due to the presence of a lipase, there was very little peak broadening of the multi-esters in this study, Therefore, the POE groups and multi-esters were also quantitated (FIG. 7). The mass balance was calculated by summing the concentrations (ppm) of the POE groups, PS80 mono-ester, and multi-esters; the precision for all mass-balance data was <10%. A negligible amount of oleic acid was observed at 40° C.

The PS80 mono-ester in multi-compendial J.T. Baker PS80 was significantly less stable than the multi-esters. This is in agreement with previous published data. While the mono-ester is very degraded, it is still possible that protection from protein aggregation or that colloidal stability is still achieved by the high amount of multi-esters remaining.

In the past, suspected protein-PS80 interactions were thought to lower the amount of initial PS80 determined in protein-containing drug products. Interestingly, this method can also determine if rapid degradation is occurring because the PS80 mono-ester concentration will decrease and there will be a corresponding increase in POE groups. If there is no increase in POE groups, it is most likely an interaction with the protein or container.

Conclusions

A novel, sensitive, and specific platform analytical method was developed for PS80 in biopharmaceutical formulations using HPLC-CAD. The method employs precipitation of the protein to mitigate potential interference that would prevent specificity and terminates any active degrading enzymes (e.g., lipases and esterases). Specificity was demonstrated using PS40, PS60, and various types of PS80. Application of the method using multiple types of IgG mAbs have provided further support of the specificity attainable by this method using fresh and severely degraded drug product.

The method was qualified to demonstrate specificity of the chromatography such that monitoring of PS80 mono-ester, POE sorbitan/isosorbide, fatty acids, and multi-ester subspecies for degradation. The qualification study concluded that method demonstrates adequate performance with respect to repeatability (2.2% RSD), intermediate precision (6.5% RSD), accuracy (101% recovery), linearity (mean $R^2$>0.999), specificity (no interfering peak observed in matrices and $R_s$≥1.5 oleic acid/PS80 mono-ester), and limit of quantification (~20 ppm for samples and 2 ppm for samples lacking protein). Investigation of severely degraded mAb drug product demonstrate that the PS80 mono-ester was degraded below the LOQ and acceptable recovery was attainable (93%). It should be noted that the decrease in PS80 mono-ester was coupled with an increase in the POE groups. The severely degraded study also enabled comparison of the specific method to an established method 5 with low specificity by quantifying all esterified PS species.

Thus in conclusion the analytical CAD method described above has been demonstrated to provide selective, sensitive, and specific quantitative and qualitative information about PS80 in biopharmaceutical products. Its potential for use as a platform method as fit-for-purpose verification was demonstrated using multiple sub-types of IgG mAbs (IgG1, IgG2, and IgG4) by employing modification to the precipitation solvent. Hence this method is a valuable tool to support stability studies for those mAbs and other biopharmaceutical drug products.

The invention claimed is:

1. A method of identifying polysorbate in a sample containing protein comprising:

(i) precipitating the protein by exposing said sample to an organic polar solvent, (ii) separating the protein from the precipitated sample by centrifuging the precipitated sample to pellet the protein and to obtain a liquid supernatant comprising polysorbates, (iii) separating subspecies of the polysorbates by subjecting the liquid supernatant to chromatography, wherein the chromatography comprises applying the liquid supernatant to a stationary phase column comprising an immobilised cyano group, and eluting the polysorbates using a mobile phase composition gradient, and (iv) detecting the separated subspecies of the polysorbates using a chromophore-lacking detector.

2. The method according to claim 1, wherein said method identifies intact polysorbate and/or degraded polysorbate products.

3. The method according to claim 2, wherein the degraded polysorbate products comprise polyoxyethylene (POE) groups.

4. The method according to claim 1, which further comprises quantitating the separated subspecies of polysorbates.

5. The method according to claim 1, wherein the protein comprises an antibody.

6. The method according to claim 1, wherein said protein is a monoclonal antibody or a fragment thereof.

7. The method according to claim 1, wherein said method detects polysorbate selected from any one of PS80, PS60, PS40 and PS20.

8. The method according to claim 1, wherein the chromophore lacking detector is a charged aerosol detector (CAD).

9. The method according to claim 1, wherein the sample comprises acetate or citrate buffer.

10. The method according to claim 1, wherein said protein in said sample is present at a concentration of from about 5 mg/ml to about 300 mg/ml.

11. The method according to claim 1, wherein said organic polar solvent is selected from methanol, isopropyl alcohol (IPA), THF, and acetone.

12. The method according to claim 1, wherein said stationary phase column is a reverse phase high-performance liquid chromatography (HPLC) column which comprises an immobilised cyano group.

13. The method according to claim 12, wherein said reverse phase HPLC column is a silica column which has a pore size of ≥80 Angstroms.

14. The method according to claim 1, wherein said mobile phase composition gradient is a mobile phase consisting of buffer A and buffer B wherein buffer A is a mixture of 0.1% Trifluoroacetic acid (TFA) in $H_2O$ and buffer B is methanol or acetonitrile.

15. The method according to claim 1, wherein said stationary phase column is a heated column which has a temperature of between about 20° C. and about 80° C.

16. The method according to claim 1, wherein:

(1) the organic polar solvent is methanol or IPA, (2) the chromatography is reverse phase HPLC, the stationary phase column is a silica column with pore size of about 300 Angstroms, and the mobile phase composition gradient consists of A and B, wherein A is a mixture of 0.1% Trifluoroacetic acid (TFA) in $H_2O$ and B is methanol or acetonitrile, and (3) the chromophore-lacking detector is a charged aerosol detector (CAD).

17. The method according to claim 1, wherein said polysorbates comprise PS40, PS60, or PS80.

18. A method for identification of a protein sample that contains from about 10 ppm about 5000 ppm of intact polysorbate, wherein the method comprises:

(a) measuring polysorbates in a sample comprising a protein, comprising (i) precipitating the protein by exposing said sample to an organic polar solvent, (ii) separating the protein from the precipitated sample by centrifuging the precipitated sample to pellet the protein and to obtain a liquid supernatant comprising polysorbates, (iii) separating subspecies of the polysorbates by subjecting the liquid supernatant to chromatography, wherein the chromatography comprises applying the liquid supernatant to a stationary phase column comprising an immobilised cyano group, and eluting the polysorbates using a mobile phase composition gradient, and (iv) detecting the separated subspecies of the polysorbates using a chromophore-lacking detector and quantitating intact polysorbates;

(b) identifying the sample from (a) which contains from about 10 ppm to about 5000 ppm of the intact polysorbates, and (c) isolating and recovering said sample identified in step (b).

19. The method according to claim 18, wherein said sample isolated and recovered in step (c) contains from about 10 ppm to about 700 ppm of intact polysorbates.

20. A protein or peptide polysorbate obtained or obtainable according to the method of claim 18.

* * * * *